United States Patent [19]

Lee et al.

[11] Patent Number: 5,475,018
[45] Date of Patent: Dec. 12, 1995

[54] 1,5-DIPHENYL PYRAZOLE COMPOUNDS FOR TREATMENT OF INFLAMMATION

[75] Inventors: Len F. Lee, St. Charles; Stephen R. Bertenshaw, Brentwood, both of Mo.

[73] Assignee: G. D. Searle & Co., Skokie, Ill.

[21] Appl. No.: 160,553

[22] Filed: Nov. 30, 1993

[51] Int. Cl.$^6$ .................. A61K 31/415; C07D 231/12
[52] U.S. Cl. ........................... 514/406; 548/377.1
[58] Field of Search ................. 548/377.1; 514/406

[56] References Cited

U.S. PATENT DOCUMENTS

| | | |
|---|---|---|
| 4,146,721 | 3/1979 | Rainer . |
| 4,914,121 | 4/1990 | Sawai et al. . |
| 5,051,518 | 9/1991 | Murray et al. . |
| 5,134,142 | 7/1992 | Matsuo et al. . |
| 5,164,381 | 11/1992 | Wachter et al. . |
| 5,298,521 | 3/1994 | Ferro . |

FOREIGN PATENT DOCUMENTS

| | | |
|---|---|---|
| 1130808 | 8/1982 | Canada . |
| 0554829A2 | 11/1993 | European Pat. Off. . |
| 7112377 | 3/1972 | Netherlands . |

*Primary Examiner*—Robert W. Ramsuer
*Attorney, Agent, or Firm*—Joseph W. Bulock; J. Timothy Keane

[57] ABSTRACT

A class of 1,5-diphenyl pyrazoles is described for the treatment of inflammation, including treatment of pain and disorders such as arthritis. Compounds of particular interest are of Formula I

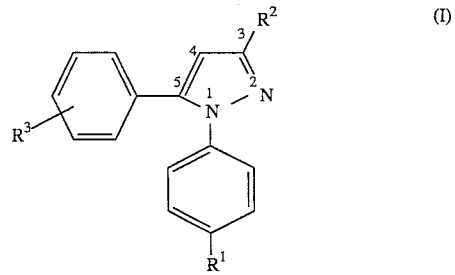

wherein $R^1$ is methylsulfonyl; wherein $R^2$ is selected from —$CF_3$, —$CF_2Cl$, —$CF_2H$, —$CF_2CF_3$ and —$CF_2CF_2CF_3$; and wherein $R^3$ is fluoro or chloro; or a pharmaceutically-acceptable salt thereof.

19 Claims, No Drawings

1,5-DIPHENYL PYRAZOLE COMPOUNDS FOR TREATMENT OF INFLAMMATION

FIELD OF THE INVENTION

This invention is in the field of anti-inflammatory pharmaceutical agents and specifically relates to compounds, compositions and methods for treating inflammation and inflammation-associated disorders, such as arthritis.

BACKGROUND OF THE INVENTION

Prostaglandins play a major role in the inflammation process and the inhibition of prostaglandin production, especially production of $PGG_2$, $PGH_2$ and $PGE_2$, has been a common target of anti-inflammatory drug discovery. However, common non-steroidal anti-inflammatory drugs (NSAIDs) that are active in reducing the prostaglandin-induced pain and swelling associated with the inflammation process are also active in affecting other prostaglandin-regulated processes not associated with the inflammation process. Thus, use of high doses of most common NSAIDs can produce severe side effects, including life threatening ulcers, that limit their therapeutic potential. An alternative to NSAIDs is the use of corticosteroids, which have even more drastic side effects, especially when long term therapy is involved.

Pyrazole compounds have been used in the treatment of inflammation. For example, U.S. Pat. No. 4,146,721 to Rainer describes 1,3-diarylpyrazole-4-acetic acid as having anti-inflammatory, antipyretic and sedative uses. U.S. Pat. No. 4,914,121 to Sawai et al describes 1,3-diarylpyrazole-4-acetic acid as having immune control uses.

Canadian Patent No. 1,130,808 describes 1,3-diphenyl pyrazoles and 1,5 diphenyl pyrazoles, including compounds having a phenyl ring optionally substituted at the 1 position with methyl, chloro or methoxy. These compounds are mentioned as having anti-inflammatory, analgesic and antipyretic properties.

EP No. 554,829, published Aug. 11, 1993, describes 1,5-diaryl pyrazoles and 1,3-diaryl pyrazoles as having anti-inflammatory activity.

Netherlands Patent No. 7,112,377 describes 1,5-diphenyl pyrazoles substituted at the "3" position with carboxylic acid derivatives. Such compounds are reported to have analgesic and anti-inflammatory activity.

U.S. Pat. No. 5,164,381 to Wachter et al describes 1,5-diphenyl pyrazole compounds which are reported to alleviate inflammation. Propanoic acid derivatives are the position "3" substituents.

U.S. Pat. No. 5,051,518 to Murray et al describes a family of (1'-methoxyphenyl-5'-aryl-3'-pyrazolyl)-N-hydroxypropanamide derivatives as being cyclooxygenase and lipoxygenase inhibitors. Pyrazole compounds, where haloalkyl radicals are the 3'-substituents, are also reported as intermediates.

U.S. Pat. No. 5,134,142 to Matsuo et al describes 1,5-diaryl pyrazoles, and specifically, 1-(4-fluorophenyl)-5-[4-(methylsulfonyl)phenyl]-3-trifluoromethyl pyrazole, as having anti-inflammatory activity.

DESCRIPTION OF THE INVENTION

A class of 1,5-diphenyl pyrazole compounds useful in treating inflammation and inflammation-related disorders is defined by Formula I:

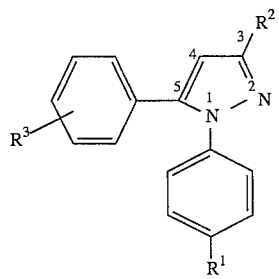

wherein $R^1$ is alkylsulfonyl; wherein $R^2$ is haloalkyl; and wherein $R^3$ is one or more groups selected from hydrido and halo; or a pharmaceutically-acceptable salt thereof.

Compounds of Formula I would be useful for the treatment of inflammation in a subject, and for treatment of other inflammation-associated disorders, such as an analgesic in the treatment of pain and headaches, or as an antipyretic for the treatment of fever. For example, compounds of Formula I would be useful to treat arthritis, including but not limited to rheumatoid arthritis, spondyloarthopathies, gouty arthritis, systemic lupus erythematosus, osteoarthritis and juvenile arthritis. Such compounds of Formula I would be useful in the treatment of asthma, bronchitis, menstrual cramps, tendinitis, bursitis, and skin related conditions such as psoriasis, eczema, burns and dermatitis. Compounds of Formula I also would be useful to treat gastrointestinal conditions such as inflammatory bowel syndrome, Crohn's disease, gastritis, irritable bowel syndrome and ulcerative colitis. Compounds of Formula I would be useful in treating inflammation in such diseases as vascular diseases, migraine headaches, periarteritis nodosa, thyroiditis, aplastic anemia, Hodgkin's disease, sclerodoma, rheumatic fever, type I diabetes, myasthenia gravis, sarcoidosis, nephrotic syndrome, Behcet's syndrome, polymyositis, hypersensitivity, conjunctivitis, gingivitis, swelling occurring after injury, myocardial ischemia, and the like. The compounds are useful as anti-inflammatory agents, such as for the treatment of arthritis, with the additional benefit of having significantly less harmful side effects.

A preferred class of compounds embraced by Formula I consists of those compounds wherein $R^1$ is methylsulfonyl; wherein $R^2$ is selected from trifluoromethyl, chlorodifluoromethyl, difluoromethyl, pentafluoroethyl and heptafluoropropyl; and wherein $R^3$ is fluoro or chloro; and pharmaceutically-acceptable salts thereof.

A more preferred class of compounds embraced by Formula I consists of those compounds wherein $R^1$ is methylsulfonyl; wherein $R^2$ is trifluoromethyl; and wherein $R^3$ is fluoro; and pharmaceutcally-acceptable salts thereof.

Within Formula I there is a subclass of high interest as represented by Formula II

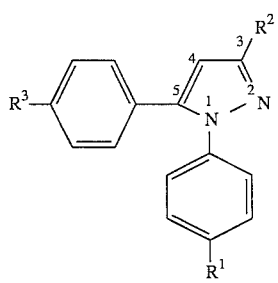

wherein $R^1$ is alkylsulfonyl; wherein $R^2$ is haloalkyl; and wherein $R^3$ is halo or hydrido; or a pharmaceutically-acceptable salt thereof.

A preferred class of compounds embraced by Formula II consists of those compounds wherein $R^1$ is methylsulfonyl; wherein $R^2$ is selected from trifluoromethyl, chlorodifluoromethyl, difluoromethyl, pentafluoroethyl and heptafluoropropyl; and wherein $R^3$ is fluoro or chloro; and pharmaceutically-acceptable salts thereof.

A more preferred class of compounds embraced by Formula II consists of those compounds wherein $R^1$ is methylsulfonyl; wherein $R^2$ is trifluoromethyl; and wherein $R^3$ is fluoro; and pharmaceutically-acceptable salts thereof.

A family of specific compounds of particular interest embraced by Formula II consists of compounds and pharmaceutically-acceptable salts thereof as follows:

1-[4-(methylsulfonyl)phenyl]-5-(4-fluorophenyl)-3-trifluoromethyl-1H-pyrazole;
1-[4-(methylsulfonyl)phenyl]-5-(4-chlorophenyl)-3-(trifluoromethyl)-1H-pyrazole;
1-[4-(methylsulfonyl)phenyl]-5-(4-bromophenyl)-3-(trifluoromethyl)-1H-pyrazole;
1-[4-(methylsulfonyl)phenyl]-5-(4-iodophenyl)-3-(trifluoromethyl)-1H-pyrazole;
1-[4-(methylsulfonyl)phenyl]-5-(phenyl)-3-(trifluoromethyl)pyrazole;
1-[4-(methylsulfonyl)phenyl]-5-(4-fluorophenyl)-3-(chlorodifluoromethyl)- 1H-pyrazole;
1-[4-(methylsulfonyl)phenyl]-5-(4-chlorophenyl)-3-(chlorodifluoromethyl)- 1H-pyrazole;
1-[4-(methylsulfonyl)phenyl]-5-(4-bromophenyl)-3-(chlorodifluoromethyl)- 1H-pyrazole;
1-[4-(methylsulfonyl)phenyl]-5-(4-iodophenyl)-3-(chlorodifluoromethyl)- 1H-pyrazole;
1-[4-(methylsulfonyl)phenyl]-5-(phenyl)-3-(chlorodifluoromethyl)- 1H-pyrazole;
1-[4-(methylsulfonyl)phenyl]-5-(4-fluorophenyl)-3-(difluoromethyl)- 1H-pyrazole;
1-[4-(methylsulfonyl)phenyl]-5-(4-chlorophenyl)-3-(difluoromethyl)- 1H-pyrazole;
1-[4-(methylsulfonyl)phenyl]-5-(4-bromophenyl)-3-(difluoromethyl)- 1H-pyrazole;
1-[4-(methylsulfonyl)phenyl]-5-(4-iodophenyl)-3-(difluoromethyl)- 1H-pyrazole;
1-[4-(methylsulfonyl)phenyl]-5-(phenyl)-3-(difluoromethyl)- 1H-pyrazole;
1-[4-(methylsulfonyl)phenyl]-5-(4-fluorophenyl)-3-(pentafluoroethyl)- 1H-pyrazole;
1-[4-(methylsulfonyl)phenyl]-5-(4-chlorophenyl)-3-(pentafluoroethyl)- 1H-pyrazole;
1-[4-(methylsulfonyl)phenyl]-5-(4-bromophenyl)-3-pentafluoroethyl)- 1H-pyrazole;
1-[4-(methylsulfonyl)phenyl]-5-(4-iodophenyl)-3-(pentafluoroethyl)- 1H-pyrazole;
1-[4-(methylsulfonyl)phenyl]-5-(phenyl)-3-(pentafluoroethyl)pyrazole;
1-[4-methylsulfonyl)phenyl]-5-(4-fluorophenyl)-3-(heptafluoropropyl)- 1H-pyrazole;
1-[4-(methylsulfonyl)phenyl]-5-(4-chlorophenyl)-3-(heptafluoropropyl)- 1H-pyrazole;
1-[4-(methylsulfonyl)phenyl]-5-(4-bromophenyl)-3-(heptafluoropropyl)- 1H-pyrazole;
1-[4-(methylsulfonyl)phenyl]-5-(4-iodophenyl)-3-(heptafluoropropyl)- 1H-pyrazole; and
1-[4-(methylsulfonyl)phenyl]-5-(phenyl)-3-(heptafluoropropyl)- 1H-pyrazole.

Where the term "alkyl" is used, either alone or within other terms such as "haloalkyl" and "alkylsulfonyl", it embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about five carbon atoms. Examples of such radicals include methyl, ethyl, n-propyl, isopropyl, n-butyl, isobutyl, sec-butyl, tert-butyl, pentyl, iso-amyl, hexyl, octyl and the like. The term "halo" means halogens such as fluorine, chlorine, bromine or iodine atoms. The term "hydrido" denotes a single hydrogen atom (H). This hydrido radical may be attached, for example, to an oxygen atom to form a hydroxyl radical or two hydrido radicals may be attached to a carbon atom to form a methylene ($-CH_2-$) radical. The term "haloalkyl" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have either a bromo, chloro or a fluoro atom within the radical. Dihalo radicals may have two of the same halo atoms or a combination of different halo radicals and polyhaloalkyl radicals may have more than two of the same halo atoms or a combination of different halo radicals. "Alkylsulfonyl" embraces alkyl radicals attached to a sulfone radical ($-SO_2-$), which in turn is attached directly to the phenyl ring of Formula I or Formula II, where alkyl is defined as above.

The present invention comprises a pharmaceutical composition for the treatment of inflammation and inflammation-associated disorders, such as arthritis, comprising a therapeutically-effective amount of a compound of Formula I in association with at least one pharmaceutically-acceptable carrier, adjuvant or diluent.

The present invention also comprises a therapeutic method of treating inflammation or inflammation-associated disorders in a subject, the method comprising administering to a subject having such inflammation or disorder a therapeutically-effective amount of a compound of Formula I.

Also included in the family of compounds of Formula I are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicyclic, salicyclic, p-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, β-hydroxybutyric, salicyclic, galactaric and galacturonic acid. Suitable pharmaceutically-acceptable base addition salts of compounds of Formula I include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of Formula I by reacting, for example, the appropriate acid or base with the compound of Formula I.

GENERAL METHOD OF SYNTHESIS

The compounds of Formula I can be prepared according to the following procedures of Schemes I–II, wherein the $R^1$–$R^3$ substitutions are as defined for Formula I, above. In step 1 of synthetic Scheme I, a halo-substituted acetophenone is treated with sodium methoxide and an ester to give the 1-(halophenyl)-4-haloalkykl-1,3-dione as detailed in the method of Reid and Calvin, *J. Amer. Chem. Soc.*, 72, 2948–2952 (1950). In step 2, the dione, as its enol form, is subsequently reacted with 4-(alkylsulfonyl)phenylhydrazine in a protic solvent, such as acetic acid or an alcohol The reaction product is a mixture of 5-(4-halophenyl)-1-[4-(alkylsulfonyl)phenyl]-3-(haloalkyl)pyrazole, which is embraced by Formula I, and its isomer, compound B, 3-(4-halophenyl)-1-[4-(alkylsulfonyl)phenyl]-5-(haloalkyl)pyrazole. Separation of the desired product from its isomer can be achieved by high performance liquid chromatography (HPLC).

none is reacted with sodium hydride in an anhydrous aprotic solvent, such as tetrahydrofuran or dimethylformamide, and subsequently reacted with gaseous haloacetonitrile to produce 3-amino-1-halophenyl-3-haloalkyl-alkenyl-1-one. In step 2, the aminoalkenylone is hydrolyzed with 6N hydrochloric acid to yield 1-(halophenyl)-3-(haloalkyl)-1,3-dione existing as its enol form. In step 3, the dione is reacted with 4-(alkylsulfonyl)phenyl hydrazine to give the desired compounds embraced by Formula I after HPLC purification.

SCHEME I

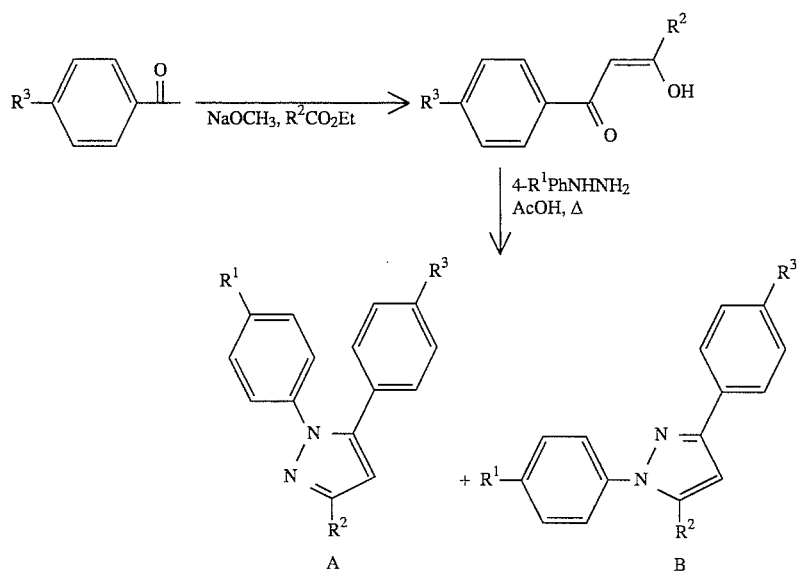

Alternatively, the compounds embraced by Formula I can be prepared, as shown in Scheme II. In step 1, haloacetophe-

SCHEME II

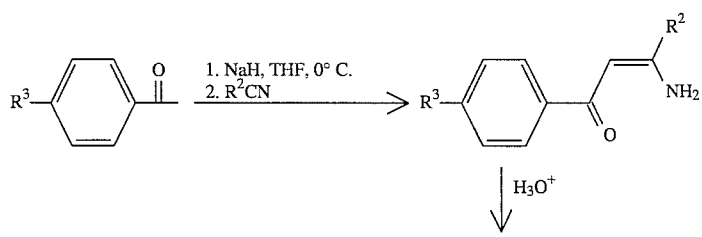

-continued
SCHEME II

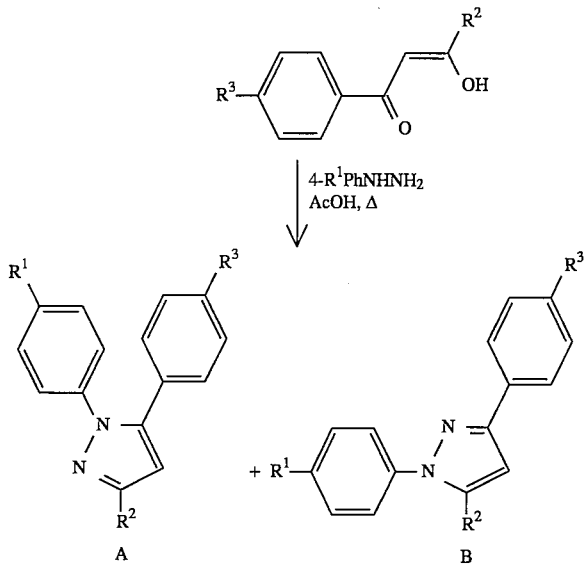

The following examples contain detailed descriptions of the methods of preparation of compounds of Formula I–II. These detailed descriptions fall within the scope, and serve to exemplify, the above described General Synthetic Procedures which form part of the invention. These detailed descriptions are presented for illustrative purposes only and are not intended as a restriction on the scope of the invention. All parts are by weight and temperatures are in Degrees centigrade unless otherwise indicated.

EXAMPLE 1

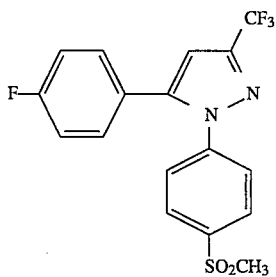

5-(4-Fluorophenyl)-1-[4-(methylsulfonyl)phenyl]-3-(trifluoromethyl)pyrazole

Step 1. Preparation of 3-amino-1-(4-fluorophenyl)-4,4,4-trifluoro-2-buten-1-one.

To a mixture of 13.2 g (0.33 mol) of 60% sodium hydride oil dispersion and 200 mL of anhydrous THF cooled in an ice bath, was added 4-fluoroacetophenone in a 30 minute period. The reaction mixture was stirred at room temperature for 15 minutes then was cooled in an ice bath. To the above mixture was passed 48.7 g of gaseous trifluoroacetonitrile over a two hour period while the reaction was monitored by gas chromatography. The reaction mixture was quenched with methanol, poured into water and extracted with methylene chloride. The methylene chloride extract was dried over $K_2CO_3$ and concentrated to give 85 g of a brown oil.

Purification by HPLC (2.5% ethyl acetate-hexane) gave 3.3 g of 4-(4-fluorophenyl)-2,6-bis(trifluoromethyl)pyrimidine in the first fraction and 30.1 g (60%) of the Step 1 intermediate in the second fraction.

Step 2. Preparation of 1-(4-fluorophenyl)-4,4,4-trifluoro-1, 3-butanedione.

To a mixture of 1.15 g (5 mmol) of the intermediate of Step 1, 20 mL of ether and 6 mL of concentrated hydrochloric acid with 10 mL of water was stirred at room temperature for 20 hours. The ether layer was separated, dried over magnesium sulfate and concentrated to give Step 2 intermediate.

Step 3. Preparation of 5-(4-Fluorophenyl)-1-[4-(methylsulfonyl)phenyl]- 3-(trifluoromethyl)pyrazole.

To Step 2 intermediate was added 0.92 g (5 mmol) of 4-(methylsulfonyl)phenylhydrazine and 20 mL of acetic acid. The reaction mixture was heated at 85° C. for 18 hours, cooled, and poured into water. The organic layer was extracted into methylene chloride (2×100 mL). The methylene chloride extract was dried over magnesium sulfate and concentrated. The residue was purified by HPLC (30% ethyl acetate-hexane). The first fraction gave 0.5 g of 3-(4-fluorophenyl)-1-[4-(methylsulfonyl)phenyl]-5-(trifluoromethyl)pyrazole, mp 158°–160° C., $^1H$ nmr ($CDCl_3$) d 8.1 (d, 2H), 7.7–7.9 (m, 4H), 7.1–7.2 (m, 3H), 3,1 (s, 3H), $^{19}F$ nmr ($CDCl_3$) d-57.41 (3F), −112.24 (1F), $^{13}C$ nmr ($CDCl_3$) d 163.3 (d, 1JCF=249.7), 151.78, 143.25, 140.89, 134.0 (q, 2JCF=40), 128.71, 127.74 (d, 3JCF=8.1), 127.36 (d, 4JCF=2.3), 119.57 (q, 1JCF=269.5), 115.95 (d, 2JCF=22.3), 107.45 (q, 3JCF=2.3), 44.52. The second fraction gave 0.5 g of 5-(4-fluorophenyl)-1-[4-(methylsulfonyl)phenyl]-3-(trifluoromethyl)pyrazole, mp 140°–142° C., $^1H$ nmr ($CDCl_3$) d 7.95 (d, 2H), 7.30 (d, 2H), 7.15 (dd, 2H), 7.05(dd, 2H), 6.79 s, 1H), 3,1 (s, 3H), $^{19}F$ nmr ($CDCl_3$) d 62.78 (3 F), −110.21 (1F), $^{13}C$ nmr ($CDCl_3$) d 163.3 (d, 1JCF=251.9), 144.27 (q, 2JCF=38.6), 144.18, 143.13, 140.15, 130.88 (d, 3JCF=8.2), 128.64, 125.69, 124.71 (d, 4JCF=3.5), 120.95 (q, 1JCF=269.4), 116.4 (d, 2JCF=22.3), 106.83, 44.42.

BIOLOGICAL EVALUATION

Rat Carrageenan Foot Pad Edema Test

The carrageenan foot edema test was performed with materials, reagents and procedures essentially as described by Winter et al (*Proc. Soc. Exp. Biol. Med.*, 111, 544 (1962)). Male Sprague-Dawley rats were selected in each group so that the average body weight was as close as possible. Rats were fasted with free access to water for over sixteen hours prior to the test. The rats were dosed orally (1 mL) with compounds suspended in vehicle containing 0.5% methylcellulose and 0.025% surfactant, or with vehicle alone. One hour later a subplantar injection of 0.1 mL of 1% solution of carrageenan/sterile 0.9% saline was administered and the volume of the injected foot was measured with a displacement plethysmometer connected to a pressure transducer with a digital indicator. Three hours after the injection of the carrageenan, the volume of the foot was again measured. The average foot swelling in a group of drug-treated animals was compared with that of a group of placebo-treated animals and the percentage inhibition of edema was determined (Otterness and Bliven, *Laboratory Models for Testing NSAIDs*, in *Non-steroidal Anti-Inflammatory Drugs*, (J. Lombardino, ed. 1985)). Results are shown in Table I.

Rat Carrageenan-induced Analgesia Test

The analgesia test using rat carrageenan was performed with materials, reagents and procedures essentially as described by Hargreaves et al (*Pain*, 32, 77 (1988)). Male Sprague-Dawley rats were treated as previously described for the Carrageenan Foot Pad Edema test. Three hours after the injection of the carrageenan, the rats were placed in a special plexiglass container with a transparent floor having a high intensity lamp as a radiant heat source, positionable under the floor. After an initial twenty minute period, thermal stimulation was begun on either the injected foot or on the contralateral uninjected foot. A photoelectric cell turned off the lamp and timer when light was interrupted by paw withdrawal. The time until the rat withdraws its foot was then measured. The withdrawal latency in seconds was determined for the control and drug-treated groups, and percent inhibition of the hyperalgesic foot withdrawal determined. Results are shown in Table I.

TABLE I

| RAT PAW EDEMA % Inhibition @ 10 mg/kg body weight | ANALGESIA % Inhibition @ 20 mg/kg body weight |
|---|---|
| Example 1  38 | 37 |

Also embraced within this invention is a class of pharmaceutical compositions comprising one or more compounds of Formula I in association with one or more non-toxic, pharmaceutically acceptable carriers and/or diluents and/or adjuvants (collectively referred to herein as "carrier" materials) and, if desired, other active ingredients. The compounds of the present invention may be administered by any suitable route, preferably in the form of a pharmaceutical composition adapted to such a route, and in a dose effective for the treatment intended. The compounds and composition may, for example, be administered intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. The active ingredient may also be administered by injection as a composition wherein, for example, saline, dextrose or water may be used as a suitable carrier.

The amount of therapeutically active compound that is administered and the dosage regimen for treating a disease condition with the compounds and/or compositions of this invention depends on a variety of factors, including the age, weight, sex and medical condition of the subject, the severity of the disease, the route and frequency of administration, and the particular compound employed, and thus may vary widely. The pharmaceutical compositions may contain active ingredient in the range of about 0.1 to 2000 mg, preferably in the range of about 0.5 to 500 mg and most preferably between about 1 and 100 mg. A daily dose of about 0.01 to 100 mg/kg body weight, preferably between about 0.1 and about 50 mg/kg body weight and most preferably from about 1 to 20 mg/kg body weight, may be appropriate. The daily dose can be administered in one to four doses per day.

For therapeutic purposes, the compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Although this invention has been described with respect to specific embodiments, the details of these embodiments are not to be construed as limitations.

What is claimed is:

1. A compound of Formula II

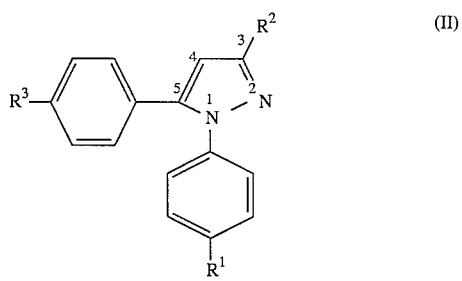

wherein $R^1$ is methylsulfonyl;

wherein $R^2$ is selected from —$CF_3$, —$CF_2Cl$, —$CF_2H$, —$CF_2CF_3$ and —$CF_2CF_2CF_3$;

wherein $R^3$ is hydrido or halo;

or a pharmaceutically-acceptable salt thereof.

2. Compound of claim 1 or a pharmaceutically-acceptable salt thereof, wherein $R^3$ is fluoro or chloro.

3. Compound of claim 1 or a pharmaceutically-acceptable salt thereof, wherein $R^1$ is methylsulfonyl; wherein $R^2$ is trifluoromethyl; and wherein $R^3$ is fluoro.

4. Compound of claim 1 selected from compounds, or their pharmaceutically-acceptable salts, of the group of compounds consisting of 1-[4-(methylsulfonyl)phenyl]-5-(4-fluorophenyl)-3-trifluoromethyl-1H-pyrazole;

1-[4-(methylsulfonyl)phenyl]-5-(4-chlorophenyl)-3-(trifluoromethyl)-1H-pyrazole;

1-[4-(methylsulfonyl)phenyl]-5-(4-bromophenyl)-3-(trifluoromethyl)-1H-pyrazole;

1-[4-(methylsulfonyl)phenyl]-5-(4-iodophenyl)-3-(trifluoromethyl)- 1H-pyrazole;

1-[4-(methylsulfonyl)phenyl]-5-(phenyl)-3-(trifluoromethyl)pyrazole;

1-[4-(methylsulfonyl)phenyl]-5-(4-fluorophenyl)-3-(chlorodifluoromethyl)- 1H-pyrazole;

1-[4-(methylsulfonyl)phenyl]-5-(4-chlorophenyl)-3-(chlorodifluoromethyl)- 1H-pyrazole;

1-[4-(methylsulfonyl)phenyl]-5-(4-bromophenyl)-3-(chlorodifluoromethyl)- 1H-pyrazole;

1-[4-(methylsulfonyl)phenyl]-5-(4-iodophenyl)-3-(chlorodifluoromethyl)- 1H-pyrazole;

1-[4-(methylsulfonyl)phenyl]-5-(phenyl)-3-(chlorodifluoromethyl)- 1H-pyrazole;

1-[4-(methylsulfonyl)phenyl]-5-(4-fluorophenyl)-3-(difluoromethyl)- 1H-pyrazole;

1-[4-(methylsulfonyl)phenyl]-5-(4-chlorophenyl)-3-(difluoromethyl)- 1H-pyrazole;

1-[4-(methylsulfonyl)phenyl]-5-(4-bromophenyl)-3-(difluoromethyl)- 1H-pyrazole;

1-[4-(methylsulfonyl)phenyl]-5-(4-iodophenyl)-3-(difluoromethyl)- 1H-pyrazole;

1-[4-(methylsulfonyl)phenyl]-5-(phenyl)-3-(difluoromethyl)- 1H-pyrazole;

1-[4-(methylsulfonyl)phenyl]-5-(4-fluorophenyl)-3-(pentafluoroethyl)- 1H -pyrazole;

1-[4-(methylsulfonyl)phenyl]-5-(4-chlorophenyl)-3-(pentafluoroethyl)- 1H-pyrazole;

1-[4-(methylsulfonyl)phenyl]-5-(4-bromophenyl)-3-(pentafluoroethyl)- 1H-pyrazole;

1-[4-(methylsulfonyl)phenyl]-5-(4-iodophenyl)-3-(pentafluoroethyl)- 1H-pyrazole;

1-[4-(methylsulfonyl)phenyl]-5-(phenyl)-3-(pentafluoroethyl)pyrazole;

1-[4-( methylsulfonyl)phenyl]-5-(4-fluorophenyl)-3-(heptafluoropropyl)- 1H-pyrazole;

1-[4-(methylsulfonyl)phenyl]-5-(4-chlorophenyl)-3-(heptafluoropropyl)- 1H -pyrazole;

1 -[4-(methylsulfonyl)phenyl]-5-(4-bromophenyl)-3-(heptafluoropropyl)- 1H-pyrazole;

1-[4-(methylsulfonyl)phenyl]-5-(4-iodophenyl)-3-(heptafluoropropyl)- 1H-pyrazole; and 1-[4-(methylsulfonyl)phenyl]-5-(phenyl)-3-(heptafluoropropyl)-1H-pyrazole.

5. Compound of claim 1 which is 1-[4-(methylsulfonyl)phenyl]-5-(4-fluorophenyl)-3-trifluoromethyl- 1H-pyrazole, or a pharmaceutically-acceptable salt thereof.

6. A pharmaceutical composition comprising a therapeutically-effective amount of a compound and a pharmaceutically-acceptable carrier or diluent, said compound selected from a family of compounds of Formula II

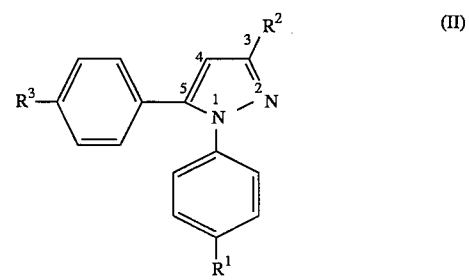

wherein $R^1$ is methylsulfonyl;

wherein $R^2$ is selected from —$CF_3$, —$CF_2Cl$, —$CF_2H$, —$CF_2CF_3$ and —$CF_2CF_2CF_3$;

wherein $R^3$ is halo or hydrido;

or a pharmaceutically-acceptable salt thereof.

7. Composition of claim 6 wherein $R^3$ is fluoro or chloro; or a pharmaceutically-acceptable salt thereof.

8. Composition of claim 7 wherein $R^1$ is methylsulfonyl; wherein $R^2$ is trifluoromethyl; and wherein $R^3$ is fluoro; or a pharmaceutically-acceptable salt thereof.

9. Composition of claim 8 wherein said anti-inflammatory compound is selected from compounds, and their pharmaceutically-acceptable salts, of the group of compounds consisting of 1-[4-(methylsulfonyl)phenyl]-5-(4-fluorophenyl)-3-trifluoromethyl- 1H-pyrazole;

1-[4-(methylsulfonyl)phenyl]-5-(4-chlorophenyl)-3-(trifluoromethyl)- 1H-pyrazole;

1-[4-(methylsulfonyl)phenyl]-5-(4-bromophenyl)-3-(trifluoromethyl)- 1H-pyrazole;

1-[4-(methylsulfonyl)phenyl]-5-(4-iodophenyl)-3-(trifluoromethyl)- 1H-pyrazole;

1-[4-(methylsulfonyl)phenyl]-5-(phenyl)-3-(trifluoromethyl)pyrazole;

1-[4-(methylsulfonyl)phenyl]-5-(4-fluorophenyl)-3-(chlorodifluoromethyl)- 1H-pyrazole;

1-[4-(methylsulfonyl)phenyl]-5-(4-chlorophenyl)-3-(chlorodifluoromethyl)- 1H-pyrazole;

1-[4-(methylsulfonyl)phenyl]-5-(4-bromophenyl)-3-(chlorodifluoromethyl)- 1H-pyrazole;

1-[4-(methylsulfonyl)phenyl]-5-(4-iodophenyl)-3-(chlorodifluoromethyl)- 1H-pyrazole;

1-[4-methylsulfonyl)phenyl]-5-(phenyl)-3-(chlorodifluoromethyl)- 1H-pyrazole;

1-[4-(methylsulfonyl)phenyl]-5-(4-fluorophenyl)-3-(difluoromethyl)- 1H-pyrazole;

1-[4-(methylsulfonyl)phenyl]-5-(4-chlorophenyl)-3-(difluoromethyl)- 1H-pyrazole;

1-[4-(methylsulfonyl)phenyl]-5-(4-bromophenyl)-3-(difluoromethyl)- 1H-pyrazole;

1-[4-(methylsulfonyl)phenyl]-5-(4-iodophenyl)-3-(difluoromethyl)- 1H-pyrazole;

1-[4-(methylsulfonyl)phenyl]-5-(phenyl)-3-(difluoromethyl)- 1H-pyrazole;

1-[4-(methylsulfonyl)phenyl]-5-(4-fluorophenyl)-3-(pentafluoroethyl)- 1H-pyrazole;

1-[4-(methylsulfonyl)phenyl]-5-(4-chlorophenyl)-3-(pentafluoroethyl)- 1H-pyrazole;

1-[4-(methylsulfonyl)phenyl]-5-(4-bromophenyl)-3-(pentafluoroethyl)- 1H-pyrazole;

1-[4-(methylsulfonyl)phenyl]-5-(4-iodophenyl)-3-(pentafluoroethyl)- 1H-pyrazole;

1-[4-(methylsulfonyl)phenyl]-5-(phenyl)-3-(pentafluoroethyl)pyrazole;

1-[4-(methylsulfonyl)phenyl]-5-(4-fluorophenyl)-3-(heptafluoropropyl)- 1H-pyrazole;

1-[4-(methylsulfonyl)phenyl]-5-(4-chlorophenyl)-3-(heptafluoropropyl)- 1H-pyrazole;

1-[4-(methylsulfonyl)phenyl]-5-(4-bromophenyl)-3-(heptafluoropropyl)- 1H-pyrazole;

1-[4-(methylsulfonyl)phenyl]-5-(4-iodophenyl)-3-(heptafluoropropyl)- 1H-pyrazole; and 1-[4-(methylsulfonyl)phenyl]-5-(phenyl)-3-(heptafluoropropyl)- 1H-pyrazole.

10. Composition of claim 9 wherein said compound is 1-[4-(methylsulfonyl)phenyl]-5-(4-fluorophenyl)- 3-trifluoromethyl-1H-pyrazole, or a pharmaceutically-acceptable salt thereof.

11. A method of treating inflammation or an inflammation-associated disorder, said method consisting of administering to a subject having said inflammation or said inflammation-associated disorder, a therapeutically-effective amount of a compound of Formula II

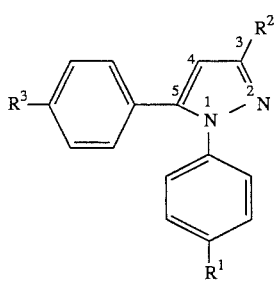

wherein $R^1$ is methylsulfonyl;

wherein $R^2$ is selected from —$CF_3$, —$CF_2Cl$, —$CF_2H$, —$CF_2CF_3$ and —$CF_2CF_2CF_3$;

wherein $R^3$ is hydrido or halo;

or a pharmaceutically-acceptable salt thereof.

12. The method of claim 11 wherein $R^3$ is fluoro or chloro; or a pharmaceutically-acceptable salt thereof.

13. The method of claim 12 wherein said compound is selected from compounds, and their pharmaceutically-acceptable salts, of the group of compounds consisting of 1-[4-(methylsulfonyl)phenyl]-5-(4-fluorophenyl)-3-trifluoromethyl- 1H-pyrazole;

1-[4-(methylsulfonyl)phenyl]-5-(4-chlorophenyl)-3-(trifluoromethyl)- 1H-pyrazole;

1-[4-(methylsulfonyl)phenyl]-5-(4-bromophenyl)-3-(trifluoromethyl)- 1H-pyrazole;

1-[4-(methylsulfonyl)phenyl]-5-(4-iodophenyl)-3-(trifluoromethyl)- 1H-pyrazole;

1-[4-(methylsulfonyl)phenyl]-5-(phenyl)-3-(trifluoromethyl)pyrazole;

1-[4-(methylsulfonyl)phenyl]-5-(4-fluorophenyl)-3-(chlorodifluoromethyl)- 1H-pyrazole;

1-[4-(methylsulfonyl)phenyl]-5-(4-chlorophenyl)-3-(chlorodifluoromethyl)- 1H-pyrazole;

1-[4-(methylsulfonyl)phenyl]-5-(4-bromophenyl)-3-(chlorodifluoromethyl)- 1H-pyrazole;

1-[4-(methylsulfonyl)phenyl]-5-(4-iodophenyl)-3-(chlorodifluoromethyl)- 1H-pyrazole;

1-[4-(methylsulfonyl)phenyl]-5-(phenyl)-3-(chlorodifluoromethyl)- 1H-pyrazole;

1-[4-(methylsulfonyl)phenyl]-5-(4-fluorophenyl)-3-(difluoromethyl)- 1H-pyrazole;

1-[4-(methylsulfonyl)phenyl]-5-(4-chlorophenyl)-3-(difluoromethyl)- 1H-pyrazole;

1-[4-(methylsulfonyl)phenyl]-5-(4-bromophenyl)-3-(difluoromethyl)- 1H-pyrazole;

1-[4-(methylsulfonyl)phenyl]-5-(4-iodophenyl)-3-(difluoromethyl)- 1H-pyrazole;

1-[4-(methylsulfonyl)phenyl]-5-(phenyl)-3-(difluoromethyl)- 1H-pyrazole;

1-[4-(methylsulfonyl)phenyl]-5-(4-fluorophenyl)-3-(pentafluoroethyl)- 1H-pyrazole;

1-[4-(methylsulfonyl)phenyl]-5-(4-chlorophenyl)-3-(pentafluoroethyl)- 1H-pyrazole;

1-[4-(methylsulfonyl)phenyl]-5-(4-bromophenyl)-3-(pentafluoroethyl)- 1H-pyrazole;

1-[4-(methylsulfonyl)phenyl]-5-(4-iodophenyl)-3-(pentafluoroethyl)- 1H-pyrazole;

1-[4-(methylsulfonyl)phenyl]-5-(phenyl)-3-(pentafluoroethyl)pyrazole;

1-[4-(methylsulfonyl)phenyl]-5-(4-fluorophenyl)-3-(heptafluoropropyl)- 1H -pyrazole;

1-[4-(methylsulfonyl)phenyl]-5-(4-chlorophenyl)-3-(heptafluoropropyl)- 1H-pyrazole;

1-[4-(methylsulfonyl)phenyl]-5-(4-bromophenyl)-3-(heptafluoropropyl)- 1H-pyrazole;

1-[4-(methylsulfonyl)phenyl]-5-(4-iodophenyl)-3-(heptafluoropropyl)- 1H-pyrazole; and 1-[4-(methylsulfonyl)phenyl]-5-(phenyl)-3-(heptafluoropropyl)- 1H-pyrazole.

14. The method of claim 12 wherein said compound is 1-[4-(methylsulfonyl)phenyl]-5-(4-fluorophenyl)- 3-trifluoromethyl-1H-pyrazole, or a pharmaceutically-acceptable salt thereof.

15. The method of claim 11 for use in treatment of inflammation.

16. The method of claim 11 for use in treatment of an inflammation-associated disorder.

17. The method of claim 16 wherein the inflammation-associated disorder is arthritis.

18. The method of claim 16 wherein the inflammation-associated disorder is pain.

19. The method of claim 16 wherein the inflammation-associated disorder is fever.

* * * * *